(12) United States Patent
Chen et al.

(10) Patent No.: US 7,687,472 B2
(45) Date of Patent: Mar. 30, 2010

(54) METHODS AND COMPOSITIONS FOR TREATING HYPERGLYCEMIC, HYPERLIPIDEMIC, OR HYPERINSULINEMIC DISORDERS

(75) Inventors: Xiaozhuo Chen, Athens, OH (US); Klaus Himmeldirk, Vincent, OH (US); Yulin Ren, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 11/575,938

(22) PCT Filed: Sep. 23, 2005

(86) PCT No.: PCT/US2005/034225

§ 371 (c)(1),
(2), (4) Date: Jul. 26, 2007

(87) PCT Pub. No.: WO2006/034468

PCT Pub. Date: Mar. 30, 2006

(65) Prior Publication Data

US 2007/0293439 A1    Dec. 20, 2007

Related U.S. Application Data

(60) Provisional application No. 60/612,354, filed on Sep. 23, 2004.

(51) Int. Cl.
*A01N 43/04* (2006.01)
*A61K 31/70* (2006.01)
(52) U.S. Cl. ........................................................ 514/35
(58) Field of Classification Search ....................... None
See application file for complete search history.

(56) References Cited

OTHER PUBLICATIONS

Khanababaee et al. Tetrahedron (1997), vol. 53, pp. 10725-10732.*

* cited by examiner

*Primary Examiner*—Patrick T Lewis
(74) *Attorney, Agent, or Firm*—Calfee, Halter and Griswold LLP

(57) ABSTRACT

Methods of treating hyperglycemic, hyperlipidemic, and hyperinsulinemic disorders are provided. Compositions for treating such disorders are also provided. The compositions can include hexose and pentose variants having acid moieties and a substituent Y linked to the six position of a hexose or the five position of the pentose.

24 Claims, 7 Drawing Sheets

METHODS AND COMPOSITIONS FOR TREATING HYPERGLYCEMIC, HYPERLIPIDEMIC, OR HYPERINSULINEMIC DISORDERS

CROSS REFERENCE TO RELATED APPLICATIONS

This invention claims priority to and any other benefit of U.S. Provisional Application No. 60/612,354, filed Sep. 23, 2004, the entirety of which is incorporated by reference herein.

FIELD OF THE INVENTION

The invention relates to methods and compositions for modulating diabetes mellitus and other disorders related to abnormal glucose, lipid and/or insulin levels in a mammalian subject.

BACKGROUND OF THE INVENTION

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996), and all references cited therein. According to the American Diabetes Association, diabetes mellitus is estimated to affect approximately 6% of the world population. Uncontrolled hyperglycemia is associated with increased and premature mortality due to an increased risk for microvascular and macrovascular diseases, including, for example, nephropathy, neuropathy, hypertension, cerebrovascular disease, and coronary heart disease. Additionally, uncontrolled hyperglycemia is associated with an increased risk of blindness due to retinopathy. Therefore, control of glucose homeostasis is an important approach for the treatment of diabetes.

There are two major forms of diabetes: Type 1 diabetes (formerly referred to as insulin-dependent diabetes mellitus or IDDM); and Type 2 diabetes (formerly referred to as non-insulin dependent diabetes mellitus or NIDDM). Type 1 diabetes is the result of an absolute deficiency of insulin, the hormone which regulates glucose utilization. This insulin deficiency is usually characterized by β-cell destruction within the Islets of Langerhans in the pancreas and absolute insulin deficiency. Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin-resistant individuals the body secretes abnormally high amounts of insulin to compensate for this defect. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes.

The majority of Type 2 diabetic patients are treated either with hypoglycemic agents, which act by stimulating release of insulin from beta cells, or with agents that enhance the tissue sensitivity of the patients to insulin, or with insulin. Sulfonylureas are examples of agents that stimulate release of insulin from beta cells. Among the agents applied to enhance tissue sensitivity to insulin, metformin is a representative example. Even though sulfonylureas are widely used in the treatment of type II diabetes, this therapy is, in most instances, not satisfactory. In a large number of type II diabetic patients sulfonylureas do not suffice to normalize blood sugar levels and the patients are, therefore, at high risk for acquiring diabetic complications. Also, many patients gradually lose the ability to respond to treatment with sulfonylureas and are, thus, gradually forced into insulin treatment. This shift of patients from oral hypoglycemic agents to insulin therapy is usually ascribed to exhaustion of the pancreatic β cells in type II diabetic patients. The guidelines for diagnosis for Type 2 diabetes, impaired glucose tolerance, and gestational diabetes have been outlined by the American Diabetes Association (see, e.g., The Expert Committee on the Diagnosis and Classification of Diabetes Mellitus, Diabetes Care, (1999) Vol 2 (Suppl 1): S5-19), which is incorporated by reference in its entirety herein.

In addition to glucose transport, insulin is intimately involved in adipogenesis, a process which involves proliferation of preadipocytes (pre-fat cells) and differentiation of preadipocytes into adipocytes (fat cells) with accumulation of fat in adipocytes. As a result of its adipogenic effect, insulin has the undesirable effect of promoting obesity in patients with type 2 diabetes. (See, Moller, D. E. (2001) Nature 414: 821-827.) Unfortunately, other anti-diabetic drugs, which are currently being used to stimulate glucose transport in patients with type 2, diabetes also possess adipogenic activity.

Syndrome X, also called metabolic syndrome, is a cluster of health conditions or disorders of the metabolism. It is marked by abdominal obesity, elevated levels of triglycerides, low levels of HDL ("good") cholesterol, high blood pressure, and/or high blood sugar levels. Recent research shows the metabolic syndrome has become increasingly common in the United States. Up to 25% (or about 50 million) of adults between the ages of 20 and 79 have at least three of these symptoms, with the prevalence approaching 50% in the elderly. It can affect anyone at any age, but it is most frequently seen in those who are significantly overweight (with most of their excess fat in the abdominal area) and inactive. When these conditions occur together, they may significantly increase the risk for developing type II diabetes and heart disease. Syndrome X can be considered as a major risk factor or a prelude for type II diabetes. Each of these disorders in Syndrome X is by itself a risk factor for other diseases. In combination, though, these disorders dramatically boost an individual's chances of developing potentially life-threatening illnesses.

Syndrome X is closely associated with a generalized metabolic disorder called insulin resistance, in which the body cannot use insulin efficiently. This is why Syndrome X is also called the insulin resistance syndrome. One group of people with insulin resistance are those with diabetes who have a defect in insulin action and cannot maintain a proper level of glucose in their blood. Another group includes people, mainly those with high blood pressure, who are nondiabetic and insulin resistant but who compensate the defect by secreting large amounts of insulin. This condition is known as hyperinsulinemia. A third group is heart attack survivors who, unlike hypertensives, have hyperinsulinemia without having abnormal glucose levels. Syndrome X is described in the Third Report of the National Cholesterol Education Program (NCEP) Expert Panel on Detection, Evaluation, and Treatment of High Blood Cholesterol in Adults (Adult Treatment Panel III, ATP III), which is incorporated by reference.

Accordingly, there remains a need in the art for anti-diabetic drugs and/or anti-adipogenic drugs to treat conditions such as diabetes, obesity, and/or Syndrome X.

SUMMARY OF THE INVENTION

In accordance with embodiments of the present invention, compounds are provided. The compound may have the formula:

wherein:

R' is selected from the pyranose and furanose forms of D-Glucose, L-Glucose, D-Mannose, L-Mannose, D-Galactose, L-Galactose, D-Allose, L-Allose, D-Altrose, L-Altrose D-Gulose, L-Gulose, D-Idose, L-Idose, D-Talose, L-Talose, D-Fructose, L-Fructose, and of the furanose forms of D-Xylose, L-Xylose, D-Lyxose, L-Lyxose, D-Arabinose, L-Arabinose, D-Ribose, L-Ribose;

X comprises an ester or ether linkage;

A comprises an acid selected from 3,4,5-trihydroxybenzoic acid, 2,3,4-trihydroxybenzoic acid, 2,3,5-trihydroxybenzoic acid, 2,4,6-trihydroxybenzoic acid, 2,3-dihydroxybenzoic acid, 2,4-dihydroxybenzoic acid, 3,4-dihydroxybenzoic acid, 3-hydroxybenzoic acid, and 4-hydroxybenzoic acid;

Y is selected from H, R, F, Cl, Br, I, $NO_2$, CN, $N_3$, $NH_2$, NHR, $NR_2$, $^{\oplus}NR_3$, SH, SR, SOH, SO—R, $SO_2H$, $SO_2$—R, O—$SO_2R$, O—$SO_2$—OH, O—$SO_2$—OR, OR, O—$NO_2$, NH—SOH, NH—SO—R, NH—$SO_2H$, NH—$SO_2$—R, and a moiety having a molecular weight of less than 300, wherein Y is attached to the 6-position of a hexose R' or the 5-position of a pentose R', and provided that Y does not equal 3,4,5-trihydroxybenzoic acid;

R comprises a hydrocarbyl group;

wherein n is 4, q is 0, 1, 2, or 3, when R' is a furanose or pyranose form of D-Glucose, L-Glucose, D-Mannose, L-Mannose, D-Galactose, L-Galactose, D-Allose, L-Allose, D-Altrose, L-Altrose D-Gulose, L-Gulose, D-Idose, L-Idose, D-Talose, L-Talose, D-Fructose, or L-Fructose; and wherein n is 3, q is 0, 1, or 2, when R' is a furanose form of D-Xylose, L-Xylose, D-Lyxose, L-Lyxose, D-Arabinose, L-Arabinose, D-Ribose, or L-Ribose.

In one example, R can comprise a $C_1$-$C_{20}$ hydrocarbyl group, a $C_1$-$C_{10}$ hydrocarbyl group, or a $C_1$-$C_5$ hydrocarbyl group. In another example, Y can comprise an electron-withdrawing moiety having a molecular weight of less than 300, or less than 200, or less than 100. In an example, Y can comprise a moiety having a molecular weight of less than 200 or less than 100.

In accordance with other embodiments of the present invention, compounds are provided. The compounds can comprise compounds having the formula:

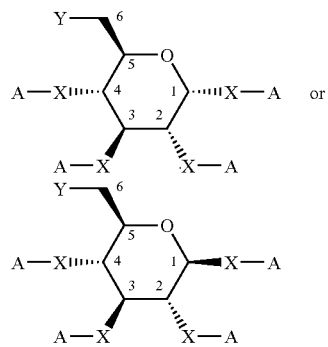

wherein:

X comprises an ester or ether linkage;

A comprises an acid selected from 3,4,5-trihydroxybenzoic acid, 2,3,4-trihydroxybenzoic acid, 2,3,5-trihydroxybenzoic acid, 2,4,6-trihydroxybenzoic acid, 2,3-dihydroxybenzoic acid, 2,4-dihydroxybenzoic acid, 3,4-dihydroxybenzoic acid, 3-hydroxybenzoic acid, and 4-hydroxybenzoic acid; and Y is selected from H, R, F, Cl, Br, I, $NO_2$, CN, $N_3$, $NH_2$, NHR, $NR_2$, $^{\oplus}NR_3$, SH, SR, SOH, SO—R, $SO_2H$, $SO_2$—R, O—$SO_2R$, O—$SO_2$-OH, O—$SO_2$—OR, OR, O—$NO_2$, NH—SOH, NH—SO—R, NH—$SO_2H$, NH—$SO_2$—R, and a moiety having a molecular weight of less than 300, provided that Y does not equal 3,4,5-trihydroxybenzoic acid; and R comprises a hydrocarbyl group.

In one example, X can comprise an ester linkage. In another example, A can comprise 3,4,5-trihydroxybenzoic acid. In yet another example, Y can comprise Cl or Br. In one example, X can comprise an ester linkage; A can comprise 3,4,5-trihydroxybenzoic acid; and Y can comprise Cl. In another example, X can comprise an ester linkage; A can comprise 3,4,5-trihydroxybenzoic acid; and Y can comprise Br. In yet another example, the compound can comprise 6-chloro-α-1,2,3,4-tetragallolyl-D-quinovopyranose.

In accordance with other embodiments, pharmaceutical compositions comprising the compounds of the present invention and at least one pharmaceutically acceptable excipient are provided. In other embodiments of the present invention, a method of treating diabetes is provided. The method can comprise administering a therapeutically effective amount of at least one compound in accordance with the present invention to a subject in need of the same, wherein the subject obtains a therapeutic benefit resulting from the administration of the at least one compound. In other embodiments, a method of treating Syndrome X is provided. The method can comprise administering a therapeutically effective amount of at least one compound according to the present invention to a subject in need of the same, wherein the subject obtains a therapeutic benefit resulting from the administration of the at least one compound.

In accordance with other embodiments of the present invention, a method treating hyperglycemia is provided. The method comprises administering a therapeutically effective amount of at least one compound in accordance with the present invention to a subject in need of the same, wherein the subject obtains a therapeutic benefit resulting from the administration of the at least one compound. In accordance with yet other embodiments, a method of treating hyperinsulinemia is provided. The method comprises administering a therapeutically effective amount of at least one compound of the present invention to a subject in need of the same, wherein the subject obtains a therapeutic benefit resulting from the administration of the at least one compound. In accordance with further embodiments of the present invention, a method of treating hyperlipidemia is provided. The method comprises administering a therapeutically effective amount of at least one compound of the present invention to a subject in need of the same, wherein the subject obtains a therapeutic benefit resulting from the administration of the at least one compound. In other embodiments, a method of treating obesity is provided. The method comprises administering a therapeutically effective amount of at least one compound of the present invention to a subject in need of the same, wherein the subject obtains a therapeutic benefit resulting from the administration of the at least one compound. In accordance with other embodiments of the present invention, a method of inhibiting differentiation of preadipocytes to adipocytes in vitro or in vivo is provided. The method comprises contacting preadipocytes with at least one compound according to present invention.

BRIEF DESCRIPTION OF THE SEVERAL VIEWS OF THE DRAWINGS

The following detailed description of embodiments of the present invention can be best understood when read in conjunction with the following drawings, where like structure is indicated with like reference numerals and in which.

DETAILED DESCRIPTION OF EMBODIMENTS OF THE INVENTION

Figure 1:
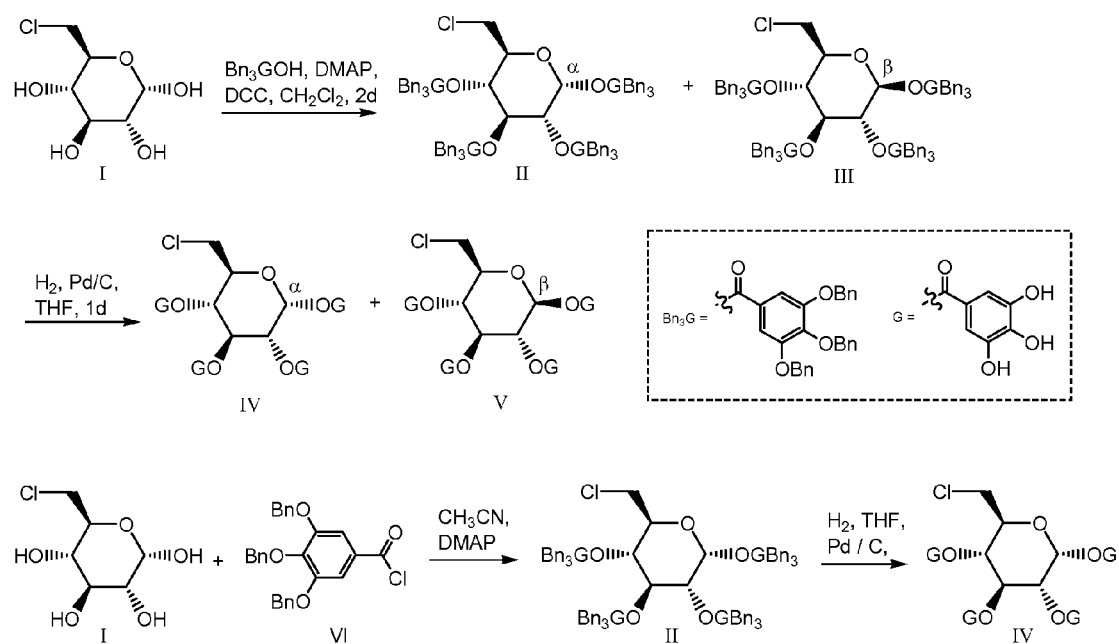
FIG. 1 illustrates the synthesis of 6-chloro-1,2,3,4-tetragalloyl-D-quinovopyranose (6Cl-TGQ) in accordance with embodiments of the present invention. 6-chloro-D-quinovopyranose was esterified with benzyl group protected gallic acid to generate II and III. The protection groups were removed by hydrogenation to yield the mixture of α- and β-isomers (IV and V). The anomers II and III can be separated into alpha and beta products by silica gel chromatography. The alpha and beta forms of 6-chloro-1,2,3,4-tetragalloyl-D-quinovopyranose (6Cl-TGQ) can be separated by reversed phase HPLC. The pure alpha isomer is synthesized by esterification with the protected acid chloride VI followed by hydrogenation and crystallization.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The present invention provides compounds, compositions and methods for treating diabetes, impaired glucose tolerance, gestational diabetes, glucose resistance, Syndrome X, obesity, and adipogenesis in a mammal, particularly a human. The compounds of the present invention are hexose and pentose variants having acid moieties and a substituent Y linked to the six position of a hexose or the five position of a pentose. In certain embodiments, the compounds have a structure corresponding to:

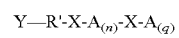

Formula I wherein:

R' is selected from the pyranose and furanose forms of D-Glucose, L-Glucose, D-Mannose, L-Mannose, D-Galactose, L-Galactose, D-Allose, L-Allose, D-Altrose, L-Altrose D-Gulose, L-Gulose, D-Idose, L-Idose, D-Talose, L-Talose, D-Fructose, L-Fructose, and of the furanose forms of D-Xylose, L-Xylose, D-Lyxose, L-Lyxose, D-Arabinose, L-Arabinose, D-Ribose, L-Ribose;

X comprises an ester or ether linkage;

A comprises an acid selected from 3,4,5-trihydroxybenzoic acid, 2,3,4-trihydroxybenzoic acid, 2,3,5-trihydroxybenzoic acid, 2,4,6-trihydroxybenzoic acid, 2,3-dihydroxybenzoic acid, 2,4-dihydroxybenzoic acid, 3,4-dihydroxybenzoic acid, 3-hydroxybenzoic acid, and 4-hydroxybenzoic acid;

Y is selected from H, R, F, Cl, Br, I, $NO_2$, CN, $N_3$, $NH_2$, NHR, $NR_2$, $^{\oplus}NR_3$, SH, SR, SOH, SO—R, $SO_2H$, $SO_2$—R, O—$SO_2R$, O—$SO_2$—OH, O—$SO_2$—OR, OR, O—$NO_2$, NH—SOH, NH—SO—R, NH—$SO_2H$, NH—$SO_2$—R, and a moiety having a molecular weight of less than 300, wherein Y is attached to the 6-position of a hexose R' or the 5-position of a pentose R', and provided that Y does not equal 3,4,5-trihydroxybenzoic acid;

R comprises a hydrocarbyl group;

wherein n is 4, q is 0, 1, 2, or 3, when R' is a furanose or pyranose form of D-Glucose, L-Glucose, D-Mannose, L-Mannose, D-Galactose, L-Galactose, D-Allose, L-Allose, D-Altrose, L-Altrose D-Gulose, L-Gulose, D-Idose, L-Idose, D-Talose, L-Talose, D-Fructose, or L-Fructose; and wherein n is 3, q is 0, 1, or 2, when R' is a furanose form of D-Xylose, L-Xylose, D-Lyxose, L-Lyxose, D-Arabinose, L-Arabinose, D-Ribose, or L-Ribose.

In accordance with an embodiment of the present invention, Y may comprise an electron withdrawing moiety having a molecular weight of less than 300. "Electron withdrawing" refers to a moiety that is more electron withdrawing than a hydrogen in place of the moiety. In accordance with another embodiment of the present invention, Y may comprise a moiety or an electron withdrawing moiety having a molecular weight of less than 200. In accordance with yet another embodiment, Y may comprise a moiety or an electron withdrawing moiety having a molecular weight of less than 100.

As used herein, the term "hydrocarbyl" is understood to include "aliphatic," "cycloaliphatic," and "aromatic." The hydrocarbyl groups are understood to include alkyl, alkenyl, alkynyl, cycloalkyl, aryl, aralkyl, and alkaryl groups. Further, "hydrocarbyl" is understood to include both non-substituted hydrocarbyl groups, and substituted hydrocarbyl groups, with the latter referring to the hydrocarbon portion bearing additional substituents, besides carbon and hydrogen. The hydrocarbyl group R may be an aliphatic, aromatic, linear, branched, cyclic, substituted or unsubstituted, and/or saturated or unsaturated, including polyunsaturated, group. In one example, R may comprise a $C_1$-$C_{20}$ hydrocarbyl group. In another example, R may comprise a $C_1$-$C_{10}$ hydrocarbyl group. In yet another example, R may comprise a $C_1$-$C_5$ hydrocarbyl group.

In accordance with an embodiment of the present invention, the compounds may have a formula corresponding to:

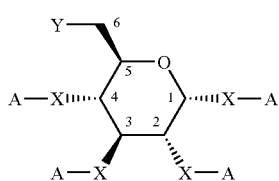

Formula II

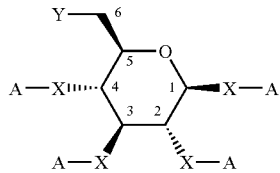

Formula III wherein:

X comprises an ester or ether linkage;

A comprises an acid selected from 3,4,5-trihydroxybenzoic acid, 2,3,4-trihydroxybenzoic acid, 2,3,5-trihydroxybenzoic acid, 2,4,6-trihydroxybenzoic acid, 2,3-dihydroxybenzoic acid, 2,4-dihydroxybenzoic acid, 3,4-dihydroxybenzoic acid, 3-hydroxybenzoic acid, and 4-hydroxybenzoic acid; and Y is selected from H, R, F, Cl, Br, I, $NO_2$, CN, $N_3$, $NH_2$, NHR, $NR_2$, $^{\oplus}NR_3$, SH, SR, SOH, SO—R, $SO_2H$, $SO_2$—R, O—$SO_2R$, O—$SO_2$—OH, O—$SO_2$—OR, OR, O—$NO_2$, NH—SOH, NH—SO—R, NH—$SO_2H$, NH—$SO_2$—R, and a moiety having a molecular weight of less than 300, provided that Y does not equal 3,4,5-trihydroxybenzoic acid; and R comprises a hydrocarbyl group.

In one example, R may comprise a $C_1$-$C_{20}$ hydrocarbyl group. In another example, R may comprise a $C_1$-$C_{10}$ hydrocarbyl group. In yet another example, R may comprise a $C_1$-$C_5$ hydrocarbyl group. In one example, X can comprise an ester linkage. In another example, A can comprise 3,4,5-trihydroxybenzoic acid. In yet another example, Y can comprise Cl or Br. In one example, X can comprise an ester linkage; A can comprise 3,4,5-trihydroxybenzoic acid; and Y can comprise Cl. In another example, X can comprise an ester linkage; A can comprise 3,4,5-trihydroxybenzoic acid; and Y can comprise Br. In yet another example, the compound can comprise 6-chloro-α-1,2,3,4-tetragalloyl-D-quinovopyranose.

The present invention also relates to pharmaceutical compositions comprising a therapeutically effective amount of one or more of the compounds of Formula I and/or Formula II and/or Formula III of the present invention or a salt or ester thereof and a pharmaceutically acceptable carrier or diluent.

The present invention also provides methods of treating diabetes in a subject by administering a pharmaceutical composition of the present invention to a subject in need of the same, wherein the subject obtains a therapeutic benefit resulting from the administration of the at least one compound. The present invention also provides methods of treating or inhibiting the development of Syndrome X in a patient comprising administering a pharmaceutical composition of the present invention to a subject in need of the same, wherein the subject obtains a therapeutic benefit resulting from the administration of the at least one compound.

The present invention also relates to use of the compounds of the present invention in a medicament for treating hyperinsulinemia, and/or hyperlipidemia, and/or hyperglycemia, wherein the subject obtains a therapeutic benefit resulting from the administration of the at least one compound. The present invention also provides methods for treating obesity in a subject by administering a pharmaceutical composition of the present invention to a subject in need of the same, wherein the subject obtains a therapeutic benefit resulting from the administration of the at least one compound. The present invention also provides methods for preventing differentiation of preadipocytes to adipocytes in vivo or in vitro comprising contacting preadipocytes with the compounds of the present invention. In one embodiment, the present therapeutic methods comprise administering a therapeutically effective amount of a one or more of the compounds of Formulas I, II, and III to a mammal in need of the same. The present methods are based at least in part on inventors' discovery that certain compounds of Formulas I, II, and III are able to stimulate glucose transport into adipocytes and prevent differentiation of preadipocytes to adipocytes.

Optionally, other agents which are used to treat or prevent diabetes, including insulin, sulfonylureas, meglitinides, biguanides (Glucophage or Metformin), thiazolidinedione (TZDs), and alpha-glucosidase inhibitors, are administered to the mammal in combination with the present compositions of Formula I and/or Formula II and/or Formula III.

The term "treating" shall be understood as referring to a subject obtaining any therapeutic benefit resulting from the administration of at least one of the compounds of the present invention, including a reduction of at least one symptom of the condition or conditions for which the at least one compound is administered or inhibition or delay of the development or progression of the condition or conditions for which the at least one compound is administered.

The term "subject in need of treatment" shall be understood as referring to a mammal having at least one symptom, at least one risk factor, or a genetic predisposition for a condition or conditions for which the compound or compounds of the present invention are administered.

The term "therapeutically effective amount" shall be understood as referring to the amount of the compound or compounds of the present invention which, alone or in combination with other drugs, provides any therapeutic benefit in the prevention, treatment, or management of at least one of the symptoms, complications, or conditions for which the compounds or compounds is administered, such as diabetes, Syndrome X, obesity, hyperinsulinemia, hyperlipidemia, and/or hyperglycemia.

The term "symptom" of diabetes, includes, but is not limited to, polyuria, polydipsia, and polyphagia, hyperinsulinemia, and hyperglycemia as used herein, incorporating their common usage.

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206-242 (McGraw-Hill, New York 1993). Cardiovascular disease can be one of several forms, including, e.g., hypertension (also referred to as high blood pressure), coronary heart disease, stroke, and rheumatic heart disease. Peripheral vascular disease refers to diseases of any of the blood vessels outside of the heart. It can be a narrowing of the blood vessels that carry blood to leg and arm muscles.

"Adipocytes" refers to fat cells.

"Preadipocytes" refers to adipocyte precursor cells that, under the action of hormones such as insulin and glucocorticoid, divide and differentiate into adipocytes.

"Adipogenesis" refers to the process by which preadipocytes divide and differentiate into adipocytes.

"Lipogenesis" refers to the process by which fat is synthesized and accumulated in adipocytes.

The term "mammal" includes, without limitation, humans, domestic animals (e.g., dogs or cats), farm animals (cows, horses, or pigs), monkeys, rabbits, mice, and laboratory animals.

Throughout this disclosure, reference will be made to compounds according to the invention. Reference to such compounds, in the specification and claims, includes esters and salts of such compounds. Thus, even if not explicitly recited, such esters and salts are contemplated, and encompassed, by reference to the compounds themselves.

Subjects

The present methods can be useful for treating mammals who have been diagnosed as having diabetes, gestational diabetes, insulin resistance, or impaired glucose tolerance. The present methods can also be useful for treating mammals exhibiting symptoms or complications of diabetes, gestational diabetes, insulin resistance, or impaired glucose tolerance, or mammals that have a genetic predisposition to or risk factor for diabetes, gestational diabetes, insulin resistance, or impaired glucose tolerance. The present methods can be useful for the in vivo or in vitro prevention of the differentiation of preadipocytes into adipocytes. The present methods can be useful for treating mammals exhibiting obesity or having a genetic predisposition or risk factors for obesity. The present methods can also be useful for treating mammals who have been diagnosed as having Syndrome X or have a genetic predisposition or risk factors for Syndrome X.

Modes of Administration

Any of the inventive compounds, employed in the methods of the invention, can be administered orally, parenterally (e.g., IV, IM, depot-IM, SQ, and depot-SQ), sublingually, via inhalation (e.g. intranasally or by mouth), intrathecally, topically, or rectally. Dosage forms known to those of skill in the art are suitable for delivery of the inventive compounds employed in the methods of the invention.

Formulations

Compositions are provided that contain therapeutically effective amounts of the inventive compounds employed in the methods of the invention. The compounds can be formulated into suitable pharmaceutical preparations such as tablets, capsules, or elixirs for oral administration or in sterile solutions or suspensions for parenteral administration. The compounds described herein can be formulated into pharmaceutical compositions using techniques and procedures well known in the art.

The inventive compound or mixture of inventive compounds employed in the methods of the present inventions, or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage is obtained. The compositions can be formulated in a unit dosage form. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more inventive compounds employed in the methods of the invention are mixed with a suitable pharmaceutically acceptable carrier. Upon mixing or addition of the compound(s), the resulting mixture may be a solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

When the compounds exhibit insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The inventive compounds employed in the methods of the invention may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, an inventive compound in lyophilized form and a suitable diluent may be provided as separated components for combination prior to use. A kit may include an inventive compound and a second therapeutic agent for co-administration. The inventive compound and second therapeutic agent may be provided as separate component parts. A kit may include a plurality of containers, each container holding one or more unit dose of the inventive compound employed in the method of the invention. The containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active inventive compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors. The active materials can also be mixed with other active materials that do not impair the desired action, or with materials that supplement the desired action. Because of the presence of high levels of proline containing proteins in the saliva, an oral formulation may be in the form of a capsule which comprises a coating to protect the inventive compounds from interacting with the saliva.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known in the art.

The inventive compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

Compounds employed in the methods of the invention may be administered enterally or parenterally. When administered orally, compounds employed in the methods of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods of the invention need to be administered only once or twice daily.

The oral dosage forms can be administered to the patient 1, 2, 3, 4, or more times daily. The inventive compounds employed in the methods of the invention can be administered either three or fewer times, or even once or twice daily. Hence, the inventive compounds employed in the methods of the invention can be administered in oral dosage form. Whatever oral dosage form is used, they can be designed so as to protect the compounds employed in the methods of the invention from the acidic environment of the stomach. Enteric coated tablets are well known to those skilled in the art. In addition, capsules filled with small spheres each coated to protect from the acidic stomach, are also well known to those skilled in the art.

Dosage

The composition of a compound of Formula I, Formula II, and/or Formula III is administered to the subject in a therapeutically effective amount. The dosages of the compounds needed to obtain a therapeutic effect can be determined in view of this disclosure by one of ordinary skill in the art by running routine trials with appropriate controls. Comparison of the appropriate treatment groups to the controls will indicate whether a particular dosage is therapeutically effective.

The amount of the compositions of the present invention required will depend upon the nature and severity of the condition being treated, and on the nature of prior treatments which the subject has undergone. Ultimately, the dosage will be determined using clinical trials. Initially, the clinician will administer doses that have been derived from animal studies.

An effective amount can be achieved by one administration of the composition. Alternatively, an effective amount is achieved by multiple administration of the composition to the subject. In vitro, the biologically effective amount, i.e., the amount sufficient to induce glucose uptake, is administered in two-fold increments, to determine the full range of activity. The efficacy of oral, subcutaneous and intravenous administration is determined in clinical studies. Although a single administration of the compositions may be beneficial, multiple doses may also be beneficial.

Methods of Determining Dosages for Stimulating Glucose Uptake in Cells

Glucose uptake activity in cells may be analyzed by measuring the uptake of 2-deoxy-D-[3H] glucose using a standard assay. Confluent 3T3-L1 adipocytes grown in 12-well plates are washed twice with serum-free DMEM and incubated with 1 mL of the same medium at 37° C. for 2 h. The cells are washed 3 times with Krebs-Ringer-Hepes (KRP) buffer and incubated with 0.9 mL KRP buffer at 37° C. for 30 min. Insulin (positive control) or the compounds of Formula I, II, or III (experimentals) are then added at pre-determined concentrations and adipocytes are incubated at 37° C. for 15 min. Glucose uptake is initiated by addition of 0.1 mL KRP buffer and 37 MBq/L 2-deoxy-D-[$^3$H] glucose and 1 mmol/L glucose as final concentrations. After 10 min, glucose uptake is terminated by washing the cells 3 times with cold PBS. The cells are lysed with 0.7 mL of 1% Triton X-100 at 37° C. for 20 min. The radioactivity retained by the cell lysates is determined by a scintillation counter. The dosage that induces the maximal glucose uptake can be selected among the experimental samples.

Methods of Determining Dosages for Stimulating Glucose Uptake in Animals

Male db/db (leptin receptor deficient) mice of 8 weeks of age may be used to determine in vivo dosages for simulating glucose uptake. Mice are divided into three to four groups depending upon how many dosages are analyzed. Ten μl of a test solution with pre-determined concentrations of the test compound or compounds is orally administered to the test mice. The negative control mice receive the same amount of water. After the administration, blood is collected from the mouse tail at various times post oral administration. The blood glucose level of a mouse at a given time post administration is measured by applying six μl of blood on a One Touch Basic Complete Diabetes Monitoring System (from Lifescan). The effective dosage range and the optimal dosage can be determined by comparison of the reduction of blood glucose levels by different dosages relative to the glucose level of the negative (water) control group.

Procedure for Determining Dosage for Preventing Adipogenesis In Vitro

To determine the effective concentration of the compounds of Formula I, II, or III to use in preventing adipogenesis in vitro, undifferentiated preadipocytes are incubated either with a differentiation-induction cocktail, comprised of 3-isobutyl-1-methylxanthine, dexamethasone, and insulin (MDI); or with MDI plus the test compound. After about 10 days MDI induces differentiation, which is clearly visible as the change from fibroblast-like preadipocytes to round-shaped, fat vesicle-containing adipocytes. The degree of the differentiation of the cells is evaluated by microscopic observation of lipid accumulation and Oil Red O staining (only triglyceride containing vesicles can be stained red), as well as by the glucose uptake activities the treated cells exhibit at the end of the incubation period. The glucose uptake assay is chosen and performed here for determination of the degree of adipocyte differentiation based on the observation that differentiated adipocytes can be induced by insulin to take up glucose whereas preadipocytes cannot.

Procedure for Determining Dosage for Preventing Adipogenesis In Vivo

To determine the in vivo anti-adipogenic effect and effective dosage of the present compounds, genetically diabetic female mice (Type II, KK-A$^y$) of five weeks of age can be used. The compound is either orally delivered or IP injected daily into the mice at various concentrations for 6 to 10 weeks. The food intake and body weight of the mice are monitored. At the end of the experiment, the parametrial adipose tissues from the treated and control mice are removed, weighed, and compared. In addition, livers of the treated and the control mice are also removed, and the lipid contents of the livers are measured. The dosage that results in largest reduction in parametrial adipose tissue and hepatic lipid contents without significantly altering food intake is considered as optimal dosage for anti-adipogenic activity of the present compounds Exemplary Methods Of Making In examples 1, 2, and 3, as illustrated in FIG. 1, the methods for the chemical syntheses of the alpha and beta forms of 6-chloro-1,2,3,4-tetragalloyl-D-quinovopyranose (IV and V) are shown. (i) 6-chloro-D-quinovopyranose (I) is synthesized from commercially available methyl α-D-glucopyranoside using a literature-known procedure (M. E. Evans, F. W. Parrish, Methods in Carbohydrate Chemistry, Vol.6, pp. 193-195 (1972)); (ii) 6-chloro-D-quinovopyranose (I) is reacted with 3,4,5-tribenzyloxybenzoic acid in a dicyclohexylcarbodiimide-mediated esterification in the presence of N,N-Dimethylaminopyridine (DMAP) in dry dichloromethane (50 mL) to yield an alpha and beta mixture of 6-chloro-1,2,3,4-tetrakis(3,4,5-tribenzyloxybenzoyl)-D-quinovopyranose (II, III); and (iii) 6-chloro-1,2,3,4-tetrakis(3,4,5-tribenzyloxybenzoyl)-D-quinovopyranose is deprotected by hydrogenation in the presence of a palladium catalyst in tetrahydrofuran to yield a mixture of alpha and beta 6-chloro-1,2,3,4-tetragalloyl-D-quinovopyranose (IV, V). (iv) The pure alpha isomer is synthesized more efficiently by esterification with the protected acid chloride VI followed by hydrogenation and crystallization.

The anomers II and III can be separated into pure alpha and beta products by silica gel chromatography. The pure alpha II and beta III can be used to form pure alpha IV or pure beta V respectively. Additionally, II and III can be used to synthesize products with other Y groups at the six position using any suitable methods. The alpha and beta forms of 6-chloro-1,2,3,4-tetragalloyl-D-quinovopyranose (6Cl-TGQ) can be separated by reversed phase HPLC.

EXAMPLES

The following examples are for purposes of illustration only and are not intended to limit the scope of the claims which are appended hereto. All references cited herein are specifically incorporated by reference.

Example 1

Synthesis of α and β-6Cl-TGQ 6-chloro-D-quinovopyranose (I) is synthesized from commercially available methyl α-D-glucopyranoside using a known procedure (M. E. Evans, F. W. Parrish, Methods in Carbohydrate Chemistry, Vol.6, pp. 193-195 (1972)).

I (100 mg, 0.50 mmol), 3,4,5-tribenzyloxybenzoic acid (1.65 g. 3.75 mmol), dicyclohexylcarbodiimide (DCC, 0.83 g, 4.00 mmol), and N,N-Dimethylaminopyridine (DMAP, 0.49 g, 4.00 mmol) were added to dry dichloromethane (50 mL). The suspension was refluxed for 24 hours. After cooling to room temperature, the urea byproduct was filtered off. The organic phase was evaporated after adding 1.3 g of silica gel. The residue was applied to a silica gel column (50 g silica gel, $CH_2Cl_2$:Toluene:Ethyl Acetate (300:100:3)). The chromatography yielded pure α- and β-isomers (II and III), and some mixed fractions of II and III. After evaporation of all product containing fractions, a highly viscous, clear, colorless oil was obtained with a yield of 0.78 g (83%). $^1$H-NMR of the α-isomer (II) in $CDCl_3$: 7.18-7.56 (68H, m), 6.89 (1H, d, 3.0 Hz), 6.37 (1H, t, 10.0 Hz), 5.74 (1H, t, 10.0 Hz), 5.64 (1H, dd, 3.0 Hz, 10.0 Hz), 4.88-5.24 (24H, m), 4.52 (1H, ddd, 20 Hz, 4.5 Hz, 10.0 Hz), 3.84 (1H, dd, 2.0 Hz, 12.5 Hz), 3.75 (1H, dd, 4.5 Hz, 12.5 Hz). $^1$H-NMR of the β-isomer (III) in $CDCl_3$: 7.18-7.51 (68H, m), 6.23 (1H, d, 8.0 Hz), 6.03 (1H, t, 10.0 Hz), 5.83 (1H, dd, 8.0 Hz, 10.0 Hz), 5.72 (1H, t, 10.0 Hz), 4.96-5.21 (24H, m), 4.31 (1H, ddd, 2 Hz, 5.5 Hz, 10 Hz), 3.88 (1H, dd, 2 Hz, 12.5 Hz), 3.74 (1H, dd, 5.5Hz, 12.5 Hz).

A mixture of II and III (0.62 g, 0.33 mmol) was dissolved in dry THF (50 mL). The solution was degassed by applying a water aspirator vacuum for about 30 seconds while stirring magnetically. The flask was then flushed with argon gas. Degassing and flushing were repeated two more times. 10% palladium on charcoal (21 mg, 0.02 mmol) was added. The mixture was degassed and then flushed with hydrogen gas. The degassing and flushing was repeated two more times. The suspension was then stirred at maximum speed at 40° C. under a hydrogen gas atmosphere at normal pressure for 24 h. The mixture was cooled, filtered through Celite, and the filtrate was evaporated. The product was dried in high vacuum at room temperature overnight.

The NMR showed a mixture of α- and β-isomers (IV and V) and some residual solvent (THF) with a yield of 274 mg (103%) of a white solid (foam). Reversed phase HPLC (Solvent A: 0.1% TFA in Acetonitrile; Solvent B: 0.1% TFA in water; C18 phase, linear gradient: 16% A to 30% A over 10 minutes, then 10 min at 30% A) leads to the pure isomers.

$^1$H-NMR of the α-isomer (IV) in acetone-$d_6$: 7.8-8.5 (12H, broad s), 7.26 (2H, s), 7.07 (2H, s), 6.99 (2H, s), 6.98 (2H, s), 6.72 (1H, d, 4.0 Hz), 6.12 (1H, t, 10.0 Hz), 5.63 (1H, t, 10.0 Hz), 5.45 (1H, dd, 4.0 Hz, 10.0 Hz), 4.62 (1H, ddd, 2.5 Hz, 5.0 Hz, 10.0 Hz), 3.87 (1H, dd, 2.0 Hz, 12.5 Hz), 3.79 (1H, dd, 5.0 Hz, 12.5 Hz). $^1$H-NMR of the β-isomer (V) in acetone-$d_6$: 7.9-8.5 (12H, broad m), 7.11 (2H, s), 7.04 (2H, s), 6.98 (2H, s), 6.95 (2H, s), 6.31 (1H, d, 8.0 Hz), 5.96 (1H, t, 10.0 Hz), 5.57 (1H, dd, 8.0 Hz, 10.0 Hz), 5.53 (1H, t, 10.0 Hz), 4.50 (1H, ddd, 2.5 Hz, 5.5 Hz, 10.0 Hz), 3.88 (1H, dd, 2.5 Hz, 12.5 Hz), 3.78 (1H, dd, 5.5 Hz, 12.5 Hz).

Example 2

Synthesis of pure 6Cl-α-TGQ

The acid chloride (7.133 g, 15.5 mmol) and 6-chloro-α-D-quinovopyranose (0.771 g, 3.89 mmol) were suspended in acetonitrile (150 mL) at room temperature. DMAP (1.99 g, 16.3 mmol) was added, and the mixture was stirred at room temperature for 18 hrs. The solvent was evaporated, and the residue was suspended in toluene (100 mL) at 60° C. Silica gel (5 g) was added. After 10 more minutes of stirring, the mixture was cooled to room temperature and then filtered through a layer of silica gel (10 g, ~1.5 cm thick). The filtrate was evaporated, and the product (II) was dried in high vacuum.

II was dissolved in dry THF (200 mL). 10% Palladium on charcoal (0.7 g, 0.66 mmol) was added. The suspension was stirred at high speed at 40° C. under a hydrogen gas atmosphere at normal pressure for 18 hrs. The mixture was cooled, filtered through Celite, and the filtrate was evaporated. The residue was taken up in water (20 mL). The mixture is evaporated at a temperature <45° C. to remove all residual organic solvent. Once more, the residue was taken up in water (20 mL) and evaporated. The residue was taken up in water (20 mL) for a third time. After 8 days at room temperature, colorless crystals of IV were filtered off, washed with water, and dried in an oil pump vacuum. Yield: 1.845 g (58%).

Example 3

Synthesis of pure 6Cl-β-TGQ

III (0.195 g, 0.10 mmol) was dissolved in dry THF (25 mL). The solution was degassed by applying a water aspirator vacuum for about 30 seconds while stirring magnetically. The flask was then flushed with argon gas. Degassing and flushing were repeated two more times. 10% Palladium on charcoal (21 mg, 0.02 mmol) was added. The mixture was degassed and then flushed with hydrogen gas. The degassing and flushing was repeated two more times. The suspension was then stirred at maximum speed at 40° C. under a hydrogen gas atmosphere at normal pressure for 24 h. The mixture was cooled, filtered through Celite, and the filtrate was evaporated. The product was dried in high vacuum at room temperature overnight. The NMR confirmed the structure of the pure β-isomer of 6Cl-TGQ, and the yield was 87 mg (105%) of a white solid (foam).

Example 4

Inducing Glucose Transport in 3T3-L1 cells

6Cl-α-TGQ and 6Cl-β-TGQ were synthesized as described above. α-TGQ was synthesized using methods analogous to the preparation of 6Cl-α-TGQ (Examples 1 and 2) starting from commercially available 6-deoxy-D-glucose. Alpha-pentagalloylglucose (α-PGG) was obtained. 3T3-L1 preadipocytes grown in 24-well plates were induced by MDI until they were differentiated into adipocytes. Adipocytes were washed twice with serum-free DMEM and incubated with 0.5 ml of the same medium in 10% $CO_2$ at 37 ° C. for 2 hours. The cells were washed 3 times with Kerbs-Ringer-HEPES (KRP) buffer (136 mM NaCl, 4.7 mM KCl, 1.25 mM $CaCl_2$, 1.25 mM $MgSO_4$ and 10 mM sodium phosphate buffer at pH 7.4) and then incubated with 0.45 ml KRP buffer at 37 ° C. for 30 minutes. Glucose transport inducing agents were individually added to the cells at predetermined concentrations and each condition was duplicated or triplicated, then the adipocytes were incubated at 37 ° C. for 15 minutes. Glucose uptake was initiated by the addition of 0.1 ml of KPR buffer supplemented with 1 µCi/ml [$^3$H] 2-deoxy-D-glucose and 1 mM cold glucose as the final concentration to the cells. After 10 min, the medium was aspirated and the plates were washed with ice-cold PBS three times to terminate the induced glucose uptake. The cells were lysed with 0.45 ml of 1% triton X-100 at 37 ° C. for 20 min. The radioactivity taken up by the cells was determined in a solution of 0.4 ml of the cell lysates and 5 ml of scintillation liquid using a scintillation counter (Beckman Instruments).

Figure 2:
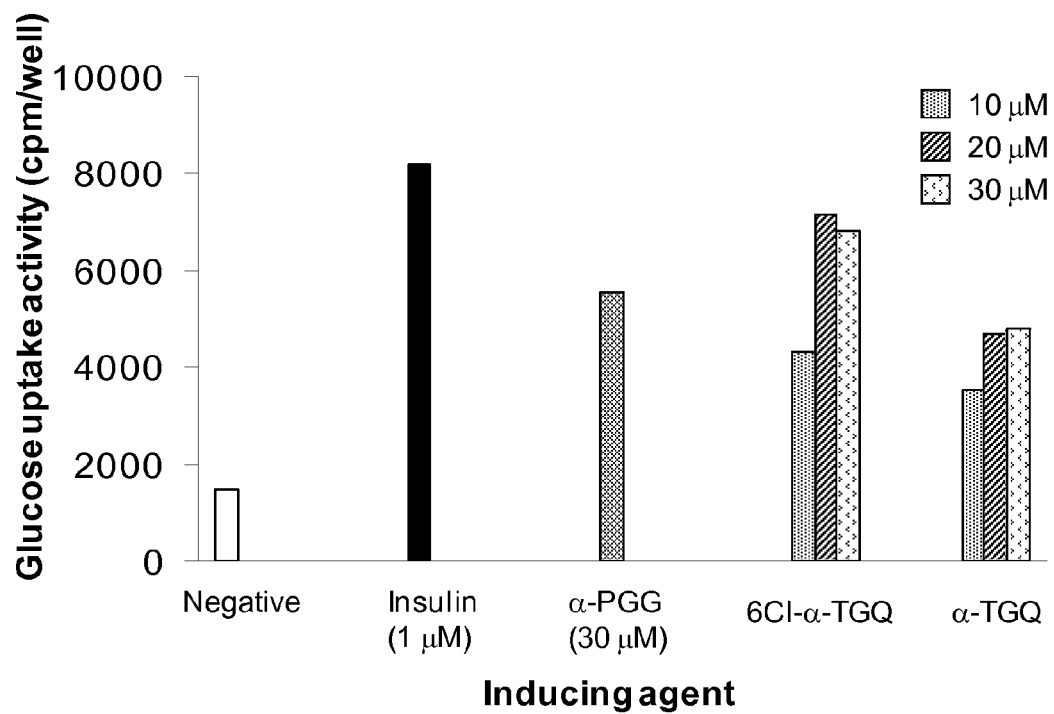
FIG. 2 illustrates that 6Cl-α-TGQ is as active as insulin in glucose transport in 3T3-L1 adipocytes. Inducing agents at various concentrations were individually added to the adipocytes for 10 min. $^3$H labeled glucose was then added to the cells for 15 min. Cells were then washed, lysed, and measured for the radioactive glucose taken up from the media. Each bar represents an average of two duplicated samples. Untreated sample, insulin-(1 μM) and α-PGG-(30 μM) treated samples served as negative and positive controls, respectively. Both 6Cl-α-TGQ and 6Cl-β-TGQ were chemically synthesized. 6Cl-α-TGQ at 30 μM transported 10% more glucose than the insulin controls. This figure also shows that 6Cl-α-TGQ is more active than pentagalloyl-α-D-glucopyranose (α-PGG), a natural antidiabetic compound, in inducing glucose transport in 3T3-L1 adipocytes. Furthermore, it indicates that α-TGQ is active as well.

Each bar of FIG. 2 represents an average of two duplicated samples. Untreated samples as well as insulin-(1 µM) and α-PGG-(30 µM) treated samples served as negative and positive controls, respectively. As can be seen in FIG. 2, 6Cl-α: TGQ is more active than α-PGG in inducing glucose transport in 3T3-L1 adipocytes.

Example 5

Glut4 Translocation Induced by 6Cl-α-TGQ

Figure 3:
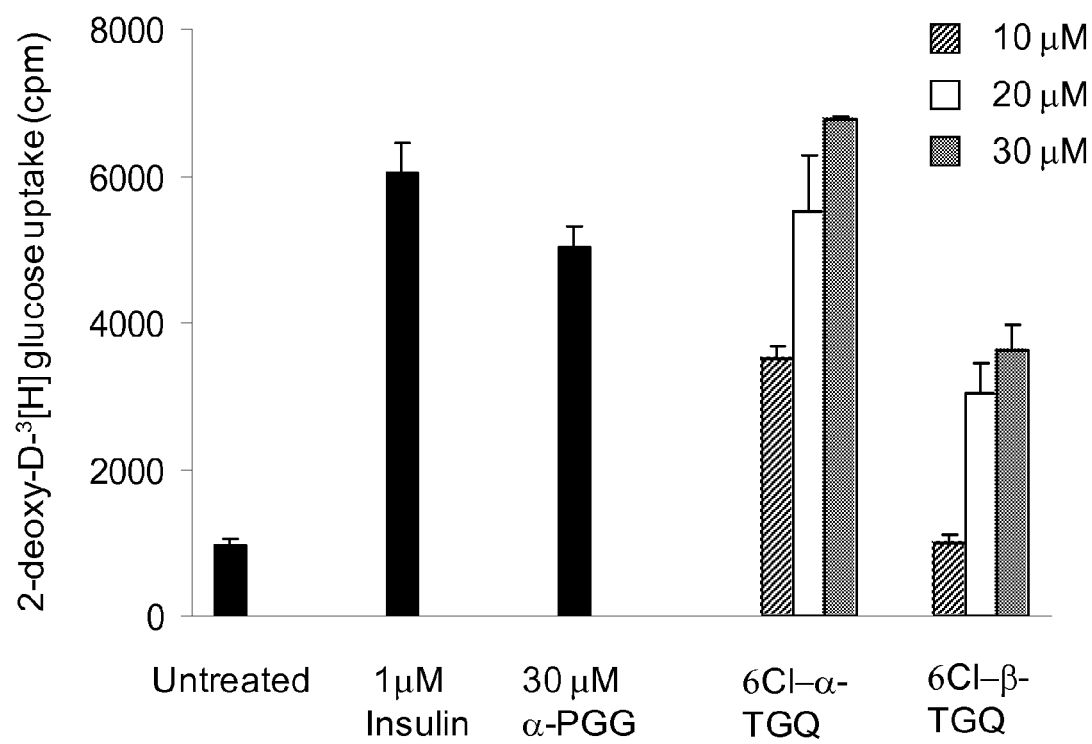
FIG. 3 illustrates induced Glut4 translocation. 3T3-L1 adipocytes were either uninduced, or induced by 1 μM insulin, or 30 μM 6Cl-α-TGQ. The treated cells were immunostained with an anti-Glut4 antibody followed with the secondary antibody (Fluorescein (FITC)-conjugated affinipure F(ad')2 fragment Donkey anti-Mouse IgG). The cells were then mounted for microscopic visualization. The immunostained cells were visualized with a Zeiss LSM510 confocal microscope at wavelength of 488 nm for excitation and 520 nm for emission. Bright staining on the cell membrane for insulin- or 6Cl-α-TGQ-induced cells (as shown by arrows) indicates induced Glut4 translocation to the cell membrane while Glut4 in uninduced cells were intracellularly localized.

3T3-L1 adipocytes were either uninduced, or induced by 1 µM of insulin, or 30 µM of 6Cl-TGQ as shown in FIG. 3. The treated cells were immunostained with an anti-Glut4 antibody followed with the secondary antibody (Fluorescein (FITC)-conjugated affinipure F(ad')2 fragment Donkey anti-Mouse IgG). The cells were then mounted for microscopic visualization. The immunostained cells were visualized with a Zeiss LSM510 confocal microscope at wavelength of 488 nm for excitation and 520 nm for emission. Bright staining on the cell membrane for insulin- or 6Cl-TGQ-induced cells indicates induced Glut4 translocation to the cell membrane while Glut4 in uninduced cells were intracellularly localized.

Example 6

Effect of 6Cl-TGQ on Adipogenesis

Figure 4:
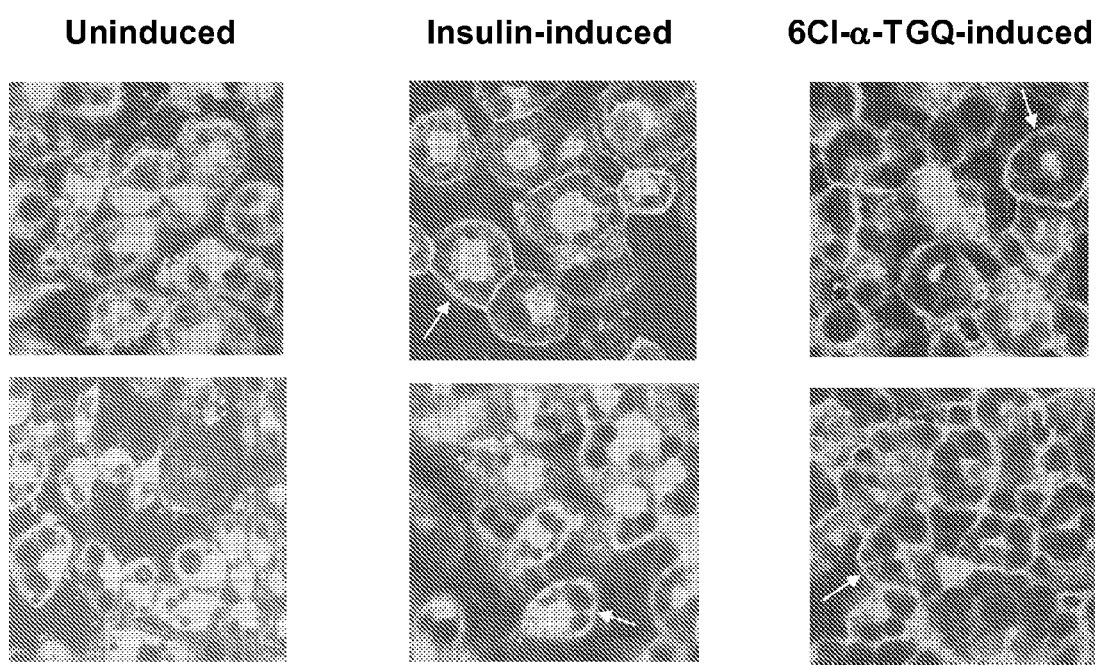
FIG. 4 illustrates adipocyte differentiation induced by MDI. 3T3-L1 preadipocytes were induced to differentiate into adipocytes by a hormonal cocktail MDI, or MDI plus 20 μM α-PGG, which is known to inhibit the differentiation, or 20 μM 6Cl-α-TGQ or 6Cl-β-TGQ. Ten days after the induction, cells were assayed for their respective ability to take up glucose from the media by a radioactive glucose uptake assay. Each sample (condition) was in triplicate. The concept that adipocyte differentiation can be indirectly measured by glucose uptake was based on the observation that only differentiated adipocytes can take up glucose through a Glut4-mediated pathway while undifferentiated preadipocytes cannot.

To test the effect of 6Cl-TGQ on adipogenesis, 3T3-L1 preadipocytes were induced to differentiate into adipocytes by a hormonal cocktail comprised of 3-isobutyl-1-methylxanthine, dexamethasone (MDI), or MDI plus 20 µM of either α-PGG, which is known to inhibit the differentiation, or 20 µM 6Cl-α-TGQ or 6Cl-β-TGQ. Ten days after the induction, cells were assayed for their respective ability to take up glucose from the media by a standard radioactive glucose uptake assay. Each sample (condition) was in triplicate. The adipocyte differentiation can be measured by glucose uptake because only differentiated adipocyte can take up glucose through Glut4-mediated pathway while undifferentiated preadipocytes cannot. The results are shown in FIG. 4, and it can be seen that 6Cl-α-TGQ and 6Cl-β-TGQ inhibit adipocyte differentiation.

Example 7

Glucose Transport Stimulatory Activity of 6Br-TGQ

6Br-α-TGQ and 6Br-β-TGQ were chemically synthesized using a preparation analogous to the preparation of 6Cl-TGQ (Examples 1, 2 and 3) starting from commercially available 6-bromo-D-glucose. 6Cl-α-TGQ was synthesized as described above. Alpha-pentagalloylglucose (α-PGG) was obtained. Confluent 3T3-L1 adipocytes were purchased from ATCC and grown in 12-well plates are washed twice with serum-free DMEM and incubated with 1 mL of the same medium at 37° C. for 2 h. The cells are washed 3 times with Krebs-Ringer-Hepes (KRP) buffer and incubated with 0.9 mL KRP buffer at 37° C. for 30 min.

Figure 5:
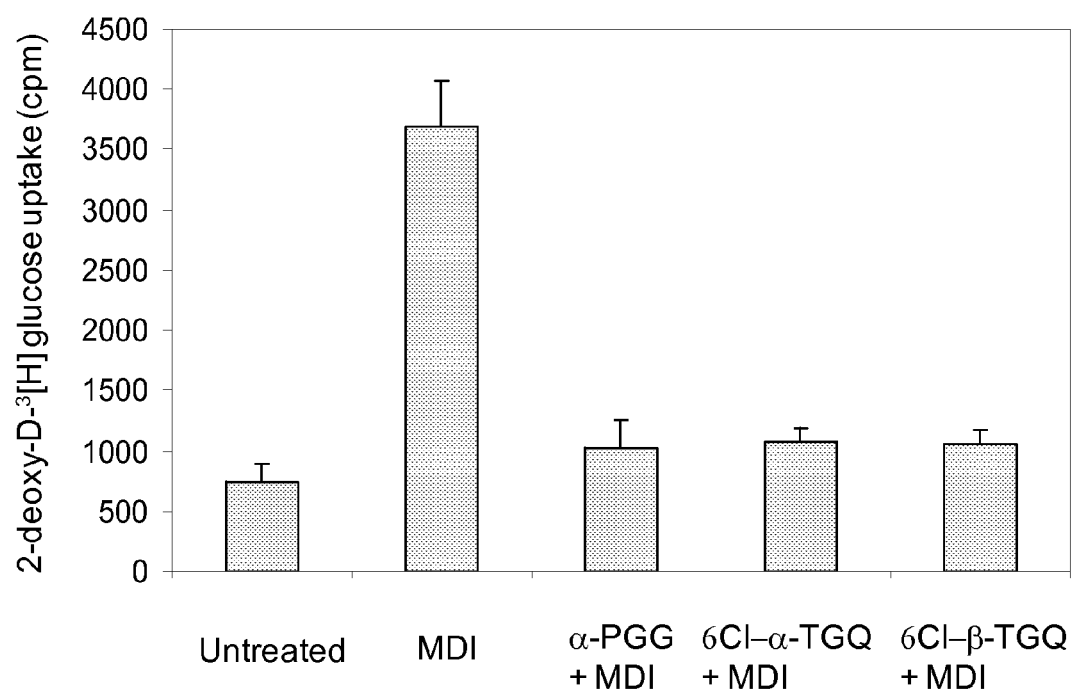
FIG. 5 illustrates glucose transport stimulatory activity in 3T3-L1 adipocytes by 6Br-α-TGQ and 6Br-β-TGQ possess glucose transport stimulatory activity in 3T3-L1 adipocytes. Two isomers of 6Br-α-TGQ and 6Br-β-TGQ were chemically synthesized and tested in 3T3-L1 adipocytes at different concentrations as shown for their respective glucose transport stimulatory activities. The glucose uptake assay indicated that 6Br-β-TGQ is more active than 6Br-α-TGQ, and is about as active as 6Cl-α-TGQ.
Figure 6:
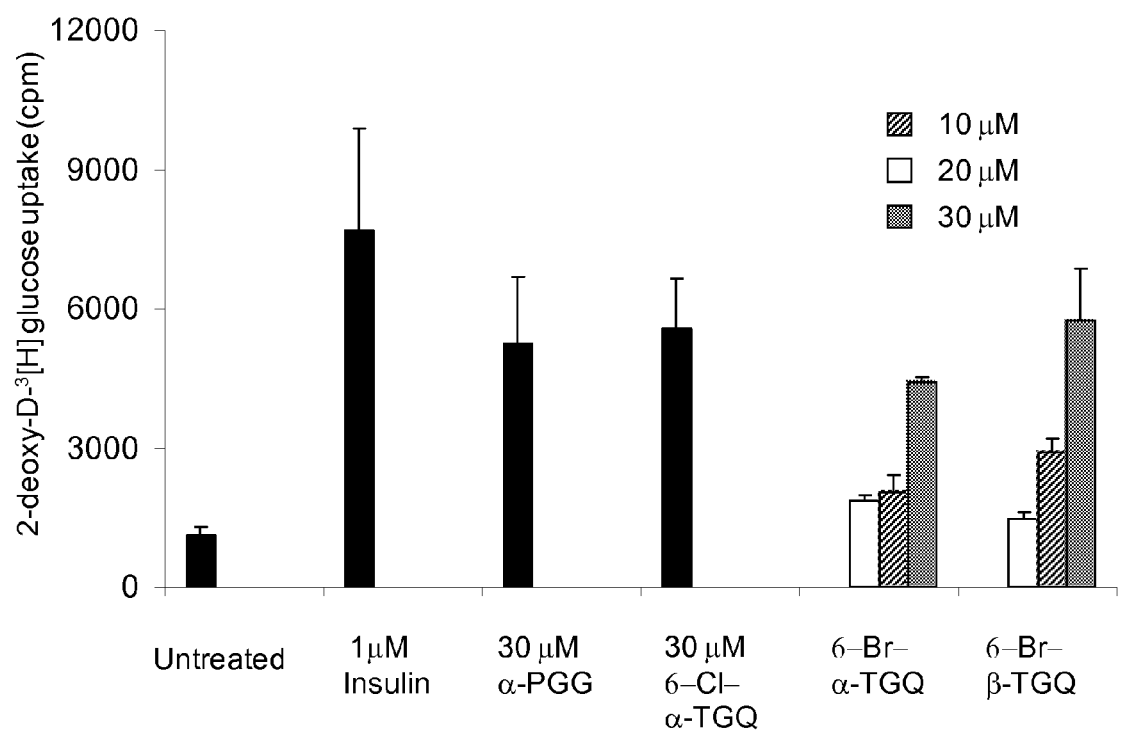
FIG. 6 illustrates that novel TGQ compounds stimulate IR and Akt phosphorylation in CHO-IR cells and Akt phosphorylation in 3T3-L1 fat cells. CHO-IR cells or 3T3-L1 adipocytes were induced under conditions as shown. Total protein was isolated from the cells and subjected SDS-PAGE and subsequently transferred to a nylon membrane. The proteins on the membrane were detected by anti-phosphorylated IR or Akt antibodies. As shown above, both 6Cl-TGQ and 6Br-TGQ can induce IR and Akt phosphorylation, similar to or the same as insulin.

Inducing agents at various concentrations were individually added to the adipocytes for 10 min, as shown in FIG. 6. Glucose uptake was initiated by addition of 0.1 mL KRP buffer and 37 MBq/L 2-deoxy-D-[$^3$H] glucose and 1 mmol/L glucose as final concentrations, and the $^3$H labeled glucose was then added to the cells for 15 min. Glucose uptake was terminated by washing the cells 3 times with cold PBS. The cells were lysed with 0.7 mL of 1% Triton X-100 at 37° C. for 20 min. The radioactivity retained by the cell lysates was determined by a scintillation counter. Each bar of FIG. 5 represents an average of two duplicated samples. Untreated, insulin-(1 μM) and α-PGG-(30 μM) treated samples served as negative and positive controls, respectively. As can be seen in FIG. 5, the glucose uptake assay indicated that 6Br-β-TGQ is more active than 6Br-α-TGQ, and is about as active as 6Cl-α-TGQ.

Example 8

Figure 7:
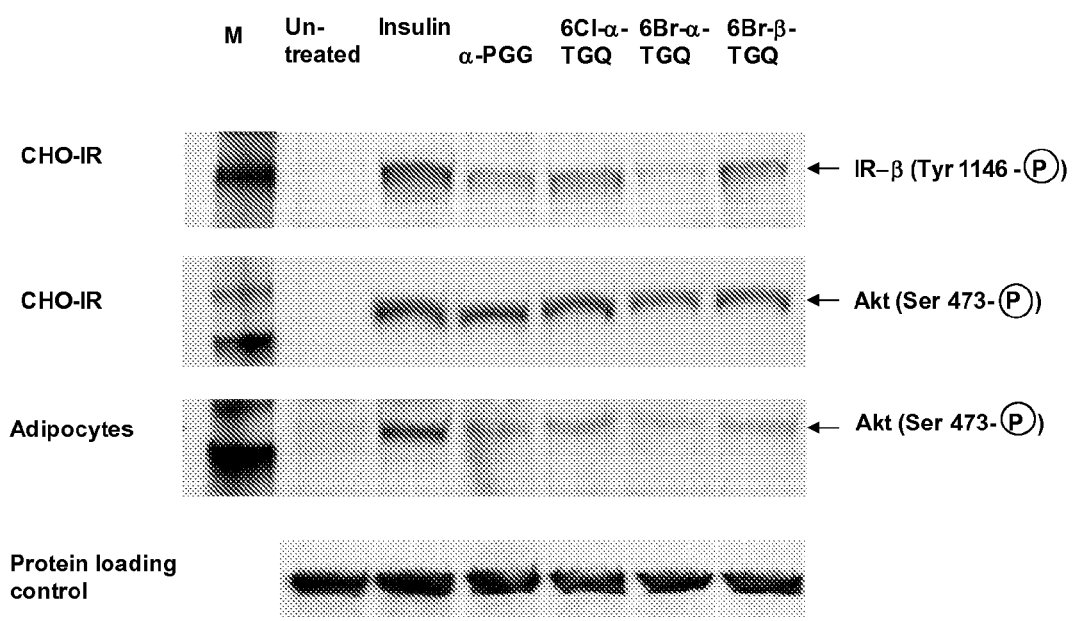
FIG. 7 shows that novel TGQ compounds stimulate IR and Akt phosphorylation in CHO-IR cells and Akt phosphorylation in 3T3-L1 fat cells. CHO-IR cells or 3T3-L1 adipocytes were induced under conditions as shown. Total protein was isolated from the cells and subjected to SDS-PAGE and subsequently transferred to a nylon membrane. The proteins on the membrane were detected by anti-phosphorylated IR or Akt antibodies. Both 6Cl-TGG and 6Br-TGQ can induce IR and Akt phosphorylation, like insulin.

TGQ Compounds Stimulate IR and Akt Phosphorylation in CHO-IR Cells and Akt Phosphorylation in 3T3-L1 Fat Cells CHO-IR cells or 3T3-L1 adipocytes were induced under conditions shown in FIG. 7. Thirty to 60 μg of total protein and the biotinylated protein marker was mixed with SDS sample buffer and heated at 95-100° C. for 5 minutes. Then, each sample and a marker were subjected to 8% SDS POLY-ACRYLAMIDE GEL ELECTROPHORESIS (SDS-PAGE). After electrophoresis, the proteins on the gel were transferred to a nitrocellulose. The nitrocellulose membrane was blocked, and then incubated with the desired primary antibody (specifically against either phosphorylated form of IR or Akt) overnight at 4° C. with gentle agitation. After overnight incubation, the membrane was washed, and then incubated with the HRP-conjugated secondary antibody for 1 hour at room temperature. Then, the membrane was washed, the proteins on the membrane were detected by a Western blotting LumiGLO system (Cell Signaling Tech, Inc) and finally visualized by exposing the membrane to an x-ray film in a cassette for a proper time, usually from 1 to 10 minutes. As shown in FIG. 6, both 6Cl-TGQ and 6Br-TGQ can induce IR and Akt phosphorylation, similar to or the same as insulin.

It will be apparent to those skilled in the art that various changes may be made without departing from the scope of the invention, which is not to be considered limited to what is described in the specification.

What is claimed is:

1. A compound having the formula:

wherein:
R' is selected from the pyranose and furanose forms of D-Glucose, L-Glucose, D-Mannose, L-Mannose, D-Galactose, L-Galactose, D-Allose, L-Allose, D-Altrose, L-Altrose D-Gulose, L-Gulose, D-Idose, L-Idose, D-Talose, L-Talose, D-Fructose, L-Fructose, and of the furanose forms of D-Xylose, L-Xylose, D-Lyxose, L-Lyxose, D-Arabinose, L-Arabinose, D-Ribose, L-Ribose;
X comprises an ester or ether linkage;
A comprises an acid selected from 3,4,5-trihydroxybenzoic acid, 2,3,4-trihydroxybenzoic acid, 2,3,5-trihydroxybenzoic acid, 2,4,6-trihydroxybenzoic acid, 2,3-dihydroxybenzoic acid, 2,4-dihydroxybenzoic acid, 3,4-dihydroxybenzoic acid, 3-hydroxybenzoic acid, and 4-hydroxybenzoic acid;
Y is selected from H, R, F, Cl, Br, I, $NO_2$, CN, $N_3$, $NH_2$, NHR, $NR_2$, $^{\oplus}NR_3$, SH, SR, SOH, SO—R, $SO_2H$, $SO_2$—R, O—$SO_2R$, O—$SO_2$—OH, O—$SO_2$—OR, OR, O—$NO_2$, NH—SOH, NH—SO—R, NH—$SO_2H$, NH—$SO_2$—R, and a moiety having a molecular weight of less than 300, wherein Y is attached to the 6-position of a hexose R' or the 5-position of a pentose R', and provided that Y does not equal 3,4,5-trihydroxybenzoic acid;
R comprises a hydrocarbyl group;
wherein n is 4, q is 0, 1, 2, or 3, when R' is a furanose or pyranose form of D-Glucose, L-Glucose, D-Mannose, L-Mannose, D-Galactose, L-Galactose, D-Allose, L-Allose, D-Altrose, L-Altrose D-Gulose, L-Gulose, D-Idose, L-Idose, D-Talose, L-Talose, D-Fructose, or L-Fructose; and
wherein n is 3, q is 0, 1, or 2, when R' is a furanose form of D-Xylose, L-Xylose, D-Lyxose, L-Lyxose, D-Arabinose, L-Arabinose, D-Ribose, or L-Ribose.

2. The compound as claimed in claim 1 wherein R comprises a $C_1$-$C_{20}$ hydrocarbyl group.

3. The compound as claimed in claim 1 wherein R comprises a $C_1$-$C_{10}$ hydrocarbyl group.

4. The compound as claimed in claim 1 wherein R comprises a $C_1$-$C_5$ hydrocarbyl group.

5. The compound as claimed in claim 1 wherein Y comprises an electron withdrawing moiety having a molecular weight of less than 300.

6. The compound as claimed in claim 1 wherein Y comprises a moiety having a molecular weight of less than 200.

7. The compound as claimed in claim 1 wherein Y comprises an electron withdrawing moiety having a molecular weight of less than 200.

8. The compound as claimed in claim 1 wherein Y comprises a moiety having a molecular weight of less than 100.

9. The compound as claimed in claim 1 wherein Y comprises an electron withdrawing moiety having a molecular weight of less than 100.

10. A compound having the formula

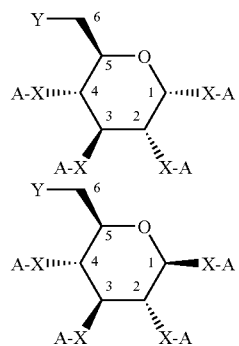

or a salt or ester thereof, wherein:
X comprises an ester or ether linkage;
A comprises an acid selected from 3,4,5-trihydroxybenzoic acid, 2,3,4-trihydroxybenzoic acid, 2,3,5-trihydroxybenzoic acid, 2,4,6-trihydroxybenzoic acid, 2,3-dihydroxybenzoic acid, 2,4-dihydroxybenzoic acid, 3,4-dihydroxybenzoic acid, 3-hydroxybenzoic acid, and 4-hydroxybenzoic acid; and
Y is selected from H, R, F, Cl, Br, I, $NO_2$, CN, $N_3$, $NH_2$, NHR, $NR_2$, $^{\oplus}NR_3$, SH, SR, SOH, SO—R, $SO_2H$, $SO_2$—R, O—$SO_2R$, O—$SO_2$—OH, O—$SO_2$—OR, OR, O—$NO_2$, NH—SOH, NH—SO—R, NH—$SO_2H$, NH—$SO_2$—R, and a moiety having a molecular weight of less than 300, provided that Y does not equal 3,4,5-trihydroxybenzoic acid; and
R comprises a hydrocarbyl group.

11. The compound as claimed in claim 10 wherein X comprises an ester linkage.

12. The compound as claimed in claim 10 wherein A comprises 3,4,5-trihydroxybenzoic acid.

13. The compound as claimed in claim 10 wherein Y comprises Cl.

14. The compound as claimed in claim 10 wherein Y comprises Br.

15. The compound as claimed in claim 10 wherein X comprises an ester linkage, A comprises 3,4,5-trihydroxybenzoic acid, and Y comprises Cl.

16. The compound as claimed in claim 10 wherein X comprises an ester linkage, A comprises 3,4,5-trihydroxybenzoic acid, and Y comprises Br.

17. The compound as claimed in claim 10 wherein the compound is 6-chloro-α-1,2,3,4-tetragallolyl-D-quinovopyranose.

18. A pharmaceutical composition comprising the compound according to claim 1 or 10 or a salt or ester thereof and at least one pharmaceutically acceptable excipient.

19. A method of treating diabetes, comprising administering a therapeutically effective amount of at least one compound according to claim 1 or 10 or a salt or ester thereof to a subject in need of the same, wherein the subject obtains a therapeutic benefit resulting from the administration of the at least one compound.

20. A method of treating Syndrome X, comprising administering a therapeutically effective amount of at least one compound according to claim 1 or 10 or a salt or ester thereof to a subject in need of the same.

21. A method of treating hyperglycemia, comprising administering a therapeutically effective amount of at least one compound according to claim 1 or 10 or a salt or ester thereof to a subject in need of the same, wherein the subject obtains a therapeutic benefit resulting from the administration of the at least one compound.

22. A method of treating hyperinsulinemia, comprising administering a therapeutically effective amount of at least one compound according to claim 1 or 10 or a salt or ester thereof to a subject in need of the same, wherein the subject obtains a therapeutic benefit resulting from the administration of the at least one compound.

23. A method of treating hyperlipidemia, comprising administering a therapeutically effective amount of at least one compound according to claim 1 or 10 or a salt or ester thereof to a subject in need of the same, wherein the subject obtains a therapeutic benefit resulting from the administration of the at least one compound.

24. A method of treating obesity, comprising administering a therapeutically effective amount of at least one compound according to claim 1 or 10 or a salt or ester thereof to a subject in need of the same, wherein the subject obtains a therapeutic benefit resulting from the administration of the at least one compound.

* * * * *